Oct. 13, 1936. D. AICARDI Plant Pat. 201
ROSE
Filed March 9, 1936
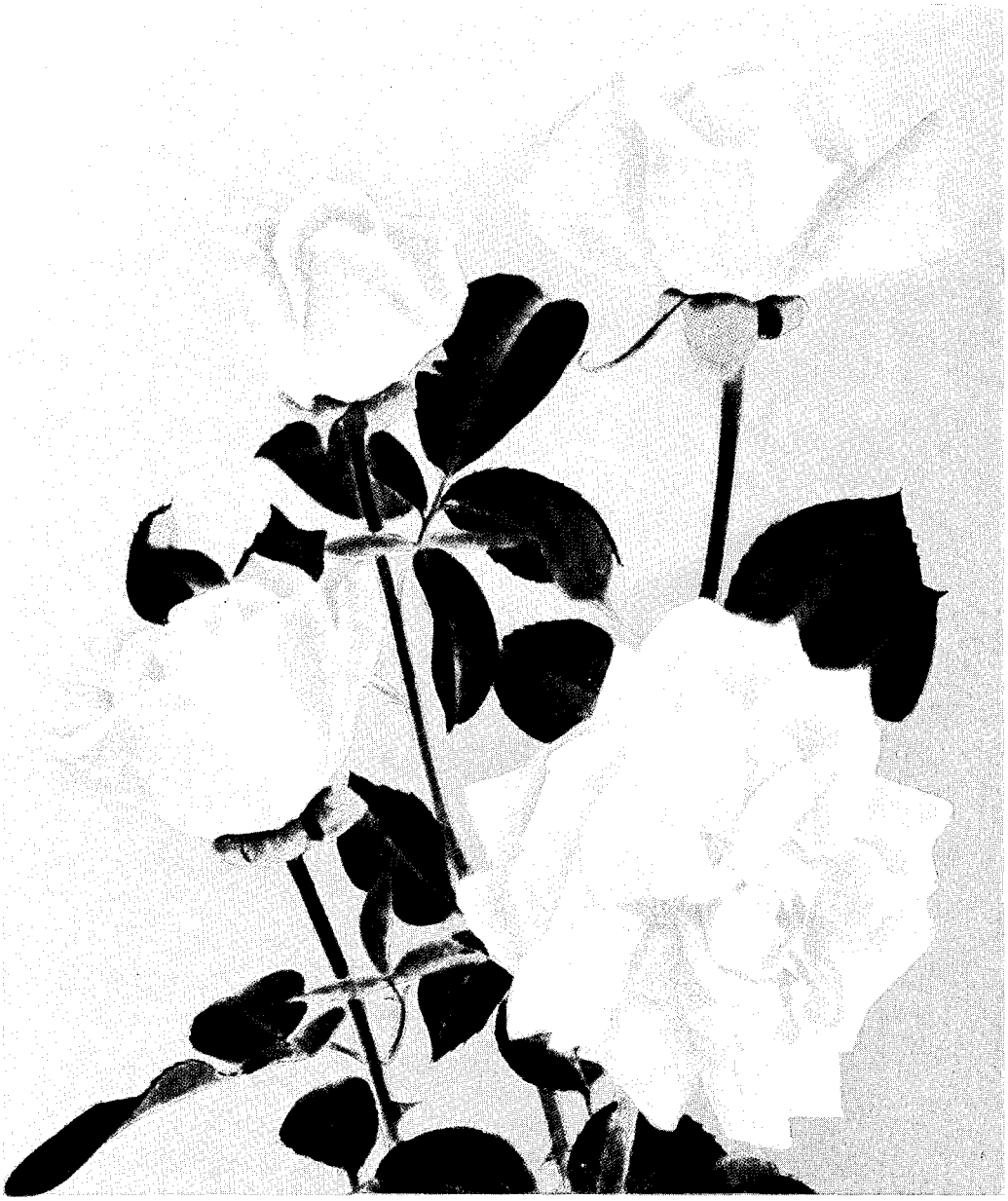
Inventor
Domenico Aicardi
By Robert Robb
Attorney Patented Oct. 13, 1936

Plant Pat. 201

UNITED STATES PATENT OFFICE

201

ROSE

Domenico Aicardi, San Remo, Italy, assignor to
Jackson & Perkins Company, Newark, N. Y.

Application March 9, 1936, Serial No. 67,981

1 Claim. (Cl. 47—61)

The present invention relates to a new and distinct variety of rose plant and is the result of a definite effort to produce a rose for cut flower purposes which would meet the difficult climatic conditions prevailing in a certain locality.

I am engaged in the business of growing roses for the cut flower market at San Remo, Italy, a place located on the slopes of high hills overlooking the Mediterranean Sea where we have normally protracted periods of drought extending from April or earlier to September. Few varieties of hybrid teas can long withstand such conditions found here so that the only solution before me was to originate my own varieties which would thrive under our climatic conditions with a view to supplying flowers of quality throughout a longer season. My new variety is the answer to the demand.

Extensive tests under glass have proved the present rose to be successful and it is considered to be a prototype of a new strain. It is already recognized in Europe as the "Aicardi strain." Florists who have grown this new variety have pronounced it to be a cut flower variety of new type and color.

In the development of this new variety, I selected the well known roses "Julien Potin" and "Sensation" as genitors because of the fact that they were well established and widely used as cut flowers in Europe, and actually did better than any other varieties under the difficult climate of Italy where the plant originated. Furthermore, I considered that these varieties, because of their wide range of color, offered a greater proclivity for new blends of tints.

I raised many thousands of seedlings from the cross and from these I selected the better ones after rigid tests and then recombined these to increase their resistance to drought and to fix this resistance as a major character. The rose herein described is the result of this development and has stood the most severe tests. It remains in full production for a long period after other varieties grown under the same conditions have become dormant and defoliated by the heat and drought.

It is to be understood from the foregoing that this new variety has been asexually reproduced and the distinctive characteristics have come true to form in the reproductions.

The following is a detailed description of this new rose, the color designations being taken from Gravereaux color chart:—

Parentage:—

Both parents were unnamed seedlings with seed ancestor Julien Potin and pollen ancestor Sensation.

Classification:—

Hybrid tea.

*Flower*

Blooming habit:—

Location where observations were made—Jackson & Perkins Company test gardens and various florists' greenhouses.

*Recurrent.*—Continuous.

Bud:—

*Size.*—Large.

*Form.*—Ovoid. Unaffected by wet or hot weather.

*Color.*—When sepals first divide—rosy salmon with touch of orange. When petals begin to unfurl—rosy salmon with touch of orange. When half blown; Inside of petals—salmon pink. Reverse of petals—salmon pink.

*Sepals.*—Smooth, curl back when bud begins to open.

*Calyx.*—Funnel shape, large, smooth. No odor when rubbed.

*Peduncle.*—Very long, rough, medium green and bronzy. Erect, heavy.

*Opening.*—Bud opens well. Is not affected by adverse conditions.

Bloom:—

*Size.*—Very large. Average size when fully expanded 4".

*Borne.*—Singly.

*Stems.*—Long, strong.

*Form.*—When first open—high center. Retains its form to the end.

*Petalage.*—Double (full but open center). Number of petals under normal conditions 35 to 50.

*Color.*—Center of flower—rose salmon. Outer petals—pink with magenta tint. Base of petals (aiglet)—yellow. Inside of petals—rosy salmon. Reverse of petals—pink with touch of orange. General tonality from a distance—salmon pink.

*Discoloration.*—General tonality at end of first and second days—rosy salmon. Third day—slightly paler.

Petals:—

*Texture.*—Thick. Unaffected by wet or hot weather.

*Appearance.*—Inside—satiny. Outside—shiny.

*Form.*—Oval and pointed.

*Arrangement.*—Informal (with "rags" in center). Petaloids—many, large and small.

*Persistence.*—Drop off cleanly.

*Fragrance.*—Moderate. Nature—tea (average hybrid tea scent).

*Lasting quality.*—On the plant and as cut flower—very long.

Genital organs:—

*Stamens, anthers.*—Large, many. Color—yellow. Arrangement—mixed with petaloids.

*Stamens, filaments (threads).*—Medium. Color—white.

*Pollen.*—Lemon yellow.

*Styles.*—Loosely separated, medium length, heavy.

*Stigmas.*—White.

*Ovaries.*—Some protruding from calyx.

Fruit:—

Variety is fertile with its own pollen.

*Form.*—Ovoid.

*Aspect.*—Smooth.

*Color at maturity.*—Orange.

*Sepals.*—Caducous (soon falling).

*Plant*

Form:—

Bush.

Growth:—

Very vigorous, upright, branching.

Foliage:—

Generally five leaflets.

*Size.*—Very large.

*Quantity.*—Abundant.

Color:—

*New foliage.*—Upper side—light green. Under side—lighter green.

*Old foliage.*—Upper side—dark green. Under side—normal green.

*Shape.*—Oval pointed.

*Texture.*—Upper side—glossy. Under side—smooth. Ribs and veins—ordinary.

*Edge.*—Serrated (saw toothed).

*Serration.*—Single, small, sharp.

*Rachis.*—Color—green and reddish.

*Stipules.*—Medium, smooth.

*Disease resistance.*—Resistant.

Wood:—

*New wood.*—Color—light green. Bark—smooth.

*Old wood.*—Color—green and brown. Bark—smooth.

Thorns:—

(Divided into thorns, prickles and short needles.)

*Thorns.*—Quantity—on main stalks from base, few. On laterals from stalk, few. Form—broad base, medium, straight and hooked downward. Color when young—green and red. Position—irregular.

*Prickles.*—Quantity—on main stalks—none. On laterals—none.

*Short needles.*—Quantity—on main stalks—none. On laterals—none.

Other traits or characters or marks of identification:—

The plant is very easily identified by its vegetation and general aspect which is unique and distinct.

I claim:

A new and distinct variety of rose plant of a new strain substantially as herein shown and described, characterized by its unusual resistance to heat and drought, its persistence of full production under climatic conditions ordinarily causing dormancy and defoliation from heat and drought, and by the color combination of its flowers.

DOMENICO AICARDI.